(12) United States Patent
Bunton et al.

(10) Patent No.: US 12,302,865 B2
(45) Date of Patent: May 20, 2025

(54) SYSTEM FOR ALERTING SERVICE ANIMALS TO PERFORM SPECIFIED TASKS

(71) Applicant: Canine Companions for Independence, Inc., Santa Rosa, CA (US)

(72) Inventors: Collette Rae Bunton, San Jose, CA (US); Brenda Schafer Kennedy, Cloverdale, CA (US); Chelsey Louise Darrow, Victor, MT (US); Flora Baird, Rohnert Park, CA (US)

(73) Assignee: Canine Companions for Independence, Inc., Santa Rosa, CA (US)

( * ) Notice: Subject to any disclaimer, the term of this patent is extended or adjusted under 35 U.S.C. 154(b) by 0 days.

(21) Appl. No.: 18/509,032

(22) Filed: Nov. 14, 2023

(65) Prior Publication Data

US 2024/0081292 A1    Mar. 14, 2024

Related U.S. Application Data

(63) Continuation of application No. 17/380,526, filed on Jul. 20, 2021, now Pat. No. 11,849,699.

(51) Int. Cl.
| | | |
|---|---|---|
| *A01K 27/00* | (2006.01) | |
| *A01K 15/02* | (2006.01) | |
| *A61B 5/00* | (2006.01) | |
| *A61B 5/024* | (2006.01) | |
| *A61B 5/16* | (2006.01) | |

(52) U.S. Cl.
CPC .......... *A01K 27/009* (2013.01); *A01K 15/021* (2013.01); *A61B 5/02438* (2013.01); *A61B 5/165* (2013.01); *A61B 5/4812* (2013.01); *A61B 2505/09* (2013.01)

(58) Field of Classification Search
CPC ............... A01K 27/009; A01K 15/021; A61B 5/02438; A61B 5/165; A61B 5/4812; A61B 2505/09
USPC ........................................................ 119/719
See application file for complete search history.

(56) References Cited

U.S. PATENT DOCUMENTS

| | | |
|---|---|---|
| 8,823,512 B2 | 9/2014 | Spector |
| 9,907,929 B2 | 3/2018 | Rink et al. |
| 9,974,903 B1 | 5/2018 | Davis et al. |
| 10,004,427 B1 | 6/2018 | Shoeb |
| 10,052,073 B2 | 8/2018 | Davis et al. |

(Continued)

*Primary Examiner* — Naomi J Small
(74) *Attorney, Agent, or Firm* — Levine Bagade Han LLP

(57) ABSTRACT

A system for alerting service animals to perform specified tasks generally includes an alert device which provides a first and a second haptic alert from an alert device worn by a service animal and a monitoring device worn by a handler. The monitoring device is programmed to monitor a physiologic parameter of the handler and has a first mode programmed to transmit a first actuation signal to the alert device when the physiologic parameter exceeds a first threshold such that the alert device provides the first haptic alert to the service animal and a second mode programmed to transmit a second actuation signal to the alert device when the physiologic parameter exceeds a second threshold such that the alert device provides the haptic alert to the service animal. The auditory alert is correlated to a first task and the second haptic alert is correlated to a second task.

15 Claims, 8 Drawing Sheets

(56) References Cited

U.S. PATENT DOCUMENTS

| | | |
|---|---|---|
| 10,328,204 B2 | 6/2019 | Davis et al. |
| 10,349,631 B2 | 7/2019 | Bonge, Jr. |
| 10,383,314 B2 | 8/2019 | Arabani et al. |
| 10,406,287 B2 | 9/2019 | Davis et al. |
| 10,765,831 B1 | 9/2020 | Skluzacek |
| 10,806,125 B1 * | 10/2020 | Wu .................. G01C 21/20 |
| 10,912,281 B2 | 2/2021 | Dayal et al. |
| 10,912,282 B2 | 2/2021 | Mckee et al. |
| 10,993,416 B2 | 5/2021 | Kapoustin et al. |
| 11,147,505 B1 | 10/2021 | Shoeb et al. |
| 2011/0245633 A1 | 10/2011 | Goldberg et al. |
| 2017/0135315 A1 | 5/2017 | Marmen et al. |
| 2017/0330295 A1 * | 11/2017 | Alden .................. A01K 11/006 |
| 2019/0223781 A1 * | 7/2019 | Arrington ............ A61B 5/7455 |
| 2019/0290217 A1 * | 9/2019 | Long ...................... A61B 5/746 |
| 2022/0165391 A1 * | 5/2022 | Cameron ............... G16H 20/70 |
| 2023/0026054 A1 | 1/2023 | Bunton et al. |

\* cited by examiner

SYSTEM FOR ALERTING SERVICE ANIMALS TO PERFORM SPECIFIED TASKS

CROSS-REFERENCE TO RELATED APPLICATIONS

This is a continuation of U.S. patent application Ser. No. 17/380,526 filed Jul. 20, 2021 (now U.S. Pat. No. 11,849,699), which is incorporated herein by reference in its entirety and for any purpose.

FIELD OF THE INVENTION

The present invention relates to systems for alerting service animals trained to perform one or more predetermined tasks. More particularly, the present invention relates to methods and apparatus for systems which are configured to monitor physiological parameters of a human and to wirelessly alert a service animal trained to perform one or more predetermined tasks correlated with the alert with respect to the human upon the physiological parameter exceeding a threshold value.

BACKGROUND OF THE INVENTION

Service animals typically include dogs (or other animals) that are individually trained to do work or perform specified tasks for the benefit of an individual with a disability, including a physical, sensory, psychiatric, intellectual, or other mental disability. Examples of such work or tasks generally include tasks such as assisting individuals who are blind or have low vision with navigation and other tasks, alerting individuals who are deaf or hard of hearing to the presence of people or sounds, pulling a wheelchair, assisting an individual during a seizure, alerting individuals to the presence of allergens, retrieving items such as medicine or the telephone, providing physical support and assistance with balance and stability to individuals with mobility disabilities, helping individuals with psychiatric and neurological disabilities by preventing or interrupting impulsive or destructive behaviors, or performing other duties.

The training for a service animal generally takes one to two years of training and such service animals are considered to be working animals and not pets. When training a service animal to facilitate or mitigate a disability of the human, the work or task the service animal has been trained to provide is directly related to the person's disability. Accordingly, the training provided to the service animal is typically specialized to address one or more particular behaviors of the person or to assist particular duties.

One such duty includes performing one or more specified tasks designed to calm or redirect their handler who may exhibit symptoms of Post Traumatic Stress Disorder (PTSD) which is a mental health condition usually triggered by experiencing or witnessing a terrifying event. Such symptoms can include flashbacks, nightmares, panic attacks, severe anxiety, self-harm, harm to others, freezing, repetitive behaviors, as well as uncontrollable thoughts about the event.

Many individuals who experience PTSD may have difficulties with adjusting and coping and can last for months or years. As PTSD can have long-term and far-reaching impacts on health and social and occupational functioning, PTSD can interfere with an individual's day-to-day social or work situations, relationships, or normal daily tasks.

Veterans and military service members, particularly those who experienced combat, as well as members of law enforcement or are part of the fire service are groups in particular which are particularly susceptible to experiencing PTSD symptoms due to the nature of their work-related experiences. Service animals which are trained to address PTSD-related episodes in their handler can be trained to interrupt an episode in their handler or distract their handler by nudging, nuzzling, or licking their handler, tugging a blanket, laying across their body, etc. The service animal may also be trained to perform any number of other specified tasks.

However, there are times when the service animal may not be aware that their handler is experiencing a PTSD episode, for instance, when situated in a crowded or noisy environment. Other times, a PTSD-related nightmare or episode may occur during nighttime when the service animal is sleeping and is unaware that their handler is experiencing an episode.

Accordingly, there exists a need for methods and apparatus which allow for a service animal to be alerted when their handler is experiencing a PTSD-related episode such that the service animal is able to perform a specified task depending upon the type of alert provided to the animal.

SUMMARY OF THE INVENTION

A system may be implemented where a handler may have one or more physiological parameters monitored by a wearable monitoring device. The monitoring device may include devices such as watches, fitness-tracking devices, bands, necklaces, patches, etc. which incorporate a processor and an optionally integrated user interface which may allow for the handler to access features or functions of the monitoring device.

The monitoring device may be configured to noninvasively sense and/or monitor any number of physiological parameters of the handler such as heartrate, blood pressure, respiration rate, etc. and may also incorporate features such as position-tracking using, for instance, accelerometers or location-tracking using, for instance, GPS tracking. In other alternative configurations, the monitoring device may be configured to be worn upon the head, such as a headband, of the handler in which case physiological parameters such as brainwaves of the handler may be detected and monitored. The monitoring device may incorporate a memory component for optionally storing such data and may also incorporate a transmitter and/or receiver which enables the transmission or receipt of data or signals through wireless protocols or any number of wired transmissions.

The handler may be paired with a service animal which is trained to interrupt PTSD-related episodes in their handler by performing any number of specified tasks. While the service animal is trained to monitor their handler for specific actions or behaviors indicative of a PTSD episode, there are times when the service animal may be distracted by the environment (e.g., loud noises, crowds, etc.), the handler may not have any outward appearance or characteristics of distress, or times when the service animal may be resting or asleep during which times the animal may be unaware of the handler's distress.

Accordingly, an alert device which is specifically wirelessly in communication with the monitoring device worn by the handler may be similarly worn by the service animal such as on a collar, integrated in a vest, patch, or otherwise secured to the body of the service animal or in proximity to the service animal. The monitoring device and the alert device may be in wireless communication through any number of wireless protocols as described herein.

In addition to being in wireless communication with the alert device, the data stored in the memory of the monitoring device may be available for transmission to a portal for long-term storage and analysis and shared with one or more third parties such as a physician, counselor, trainer, etc. for receiving the data for monitoring, adjustments, and research as it relates to efficacy and decrease in PTSD-related symptomatology. This data may be transmitted on a regulated schedule or it may transmitted or obtained by the one or more third parties, for example, on an as-needed basis or a periodic basis such as a weekly or monthly basis. In either case, the data may be used for various purposes such as assessing for the effectiveness of the service animal's training in distracting their handler from an episode or for other reasons such as research purposes.

The monitoring device may be worn by the handler while the alert device may be worn by the service animal. While any number of physiological parameters of the handler may be monitored, one parameter may include the heartrate of the handler which may be detected and monitored using any number of mechanisms commonly integrated into devices such as optical heartrate monitors worn by users.

As the monitoring device monitors the handler's heartrate, the monitoring device may remain in a holding status so long as the detected heartrate falls within a normal range. In the event that the heartrate of the handler becomes elevated for a period of time, which falls outside of a predetermined range and his/her position or location remains static, this may be indicative of the handler experiencing a PTSD-episode. In such a situation, the monitoring device may be triggered to send a signal wirelessly to the alert device worn by the service animal. The signal may be received by the alert device which may then activate one of several predetermined alerts (depending upon the mode of the monitoring device 12) as an indicator (e.g., awake or alert) to the service animal to perform one or more tasks or steps which are specifically correlated to the type of alert activated by the alert device.

A third-party trainer may initially have access to the monitoring device as well as the alert device for training purposes by which the trainer may manually operate the various predetermined alerts in order to train the service animal. In this manner, the trainer may train the service animal to perform a specified task which is correlated to a specified alert received by the service animal.

When the handler sleeps, the monitoring device in nighttime mode may monitor the heartrate of the handler. If the handler has a heartrate that exceeds the predetermined threshold level for a period of time beyond the preset grace time, the monitoring device may be programmed to send an actuation signal to the alert device. If the monitored heartrate does not exceed the predetermined threshold level or if an elevated heartrate does not extend beyond the preset grace time, the monitoring device may continue to monitor the handler's heartrate.

However, once the actuation signal has been sent to the alert device worn by the service animal, the alert device may emit an audible alert to the service animal so that the service animal may perform the specified nighttime task or tasks for the handler. The alert device may continue to provide the audible alert for a set period of time, e.g., one minute, or until the device is reset by the handler.

When the handler is awake, the monitoring device in daytime mode may monitor the heartrate of the handler. If the handler has a heartrate that exceeds the predetermined threshold level for a period of time beyond the preset grace time, the monitoring device may be programmed to send an actuation signal to the alert device. If the monitored heartrate does not exceed the predetermined threshold level or if an elevated heartrate does not extend beyond the preset grace time, the monitoring device may continue to monitor the handler's heartrate.

Once the actuation signal has been sent to the alert device, the alert device may transmit a haptic alert to the service animal so that the service animal may perform the specified daytime task or tasks for the handler. The alert device may continue to provide the haptic alert for a set period of time, e.g., one minute, or until the device is reset by the handler.

In one variation, the system for alerting a service animal may generally comprise an alert device configured to be worn by a service animal and to provide at least a first haptic alert and a second haptic alert from an alert device to the service animal, a monitoring device configured to be worn by a handler and where the monitoring device is programmed to monitor a physiologic parameter of the handler via at least one sensor, wherein the monitoring device in a first mode is programmed to transmit a first actuation signal to the alert device when the physiologic parameter exceeds a first predetermined threshold level such that the alert device provides the first haptic alert to the service animal whereby the first haptic alert is correlated to a first task to be completed by the service animal, and wherein the monitoring device in a second mode is programmed to transmit a second actuation signal to the alert device when the physiologic parameter exceeds a second predetermined threshold level such that the alert device provides the second haptic alert to the service animal whereby the haptic alert is correlated to a second task to be completed by the service animal.

In another variation, one method of alleviating anxiety in a handler may generally comprise monitoring a physiologic parameter of the handler via at least one sensor located along a monitoring device worn by the handler, determining whether the physiologic parameter exceeds a first predetermined threshold level in a first mode of the monitoring device or exceeds a second predetermined threshold level in a second mode of the monitoring device, transmitting a first actuation signal to an alert device worn by a service animal when in the first mode and when the physiologic parameter exceeds the first predetermined threshold level, transmitting a second actuation signal to the alert device when in the second mode and when the physiologic parameter exceeds the second predetermined threshold, actuating a first haptic alert from the alert device when the first actuation signal is received by the alert device such that the service animal performs a first task correlated to the first haptic alert, and actuating a second haptic alert from the alert device when the second actuation signal is received by the alert device such that the service animal performs a second task correlated to the second haptic alert.

In another variation, another method of alleviating a PTSD-related episode in a handler may generally comprise monitoring a heartrate of the handler via at least one sensor located along a monitoring device worn by the handler, determining whether the heartrate exceeds a first predetermined threshold level in a nighttime mode of the monitoring device or exceeds a second predetermined threshold level in a daytime mode of the monitoring device, transmitting a first actuation signal to an alert device worn by a service animal when in the nighttime mode and when the heartrate exceeds the first predetermined threshold level, transmitting a second actuation signal to the alert device when in the daytime mode and when the heartrate exceeds the second predetermined threshold, actuating a first haptic alert from the alert device when the first actuation signal is received by the alert device such that the service animal performs a first task correlated to the auditory alert to disrupt the PTSD-related episode, and actuating a second haptic alert from the alert device when the second actuation signal is received by the alert device such that the service animal performs a second task correlated to the second haptic alert to disrupt the PTSD-related episode.

In yet another variation, a system for alerting a service animal may generally comprise an alert device configured to be worn by a service animal and to provide at least an auditory alert and a haptic alert from an alert device to the service animal, a monitoring device configured to be worn by a handler and where the monitoring device is programmed to monitor a physiologic parameter of the handler via at least one sensor, wherein the monitoring device in a first mode is programmed to transmit a first actuation signal to the alert device when the physiologic parameter exceeds a first predetermined threshold level such that the alert device provides the auditory alert to the service animal whereby the auditory alert is correlated to a first task to be completed by the service animal, and wherein the monitoring device in a second mode is programmed to transmit a second actuation signal to the alert device when the physiologic parameter exceeds a second predetermined threshold level such that the alert device provides the haptic alert to the service animal whereby the haptic alert is correlated to a second task to be completed by the service animal.

DETAILED DESCRIPTION OF THE INVENTION

Figure 1:
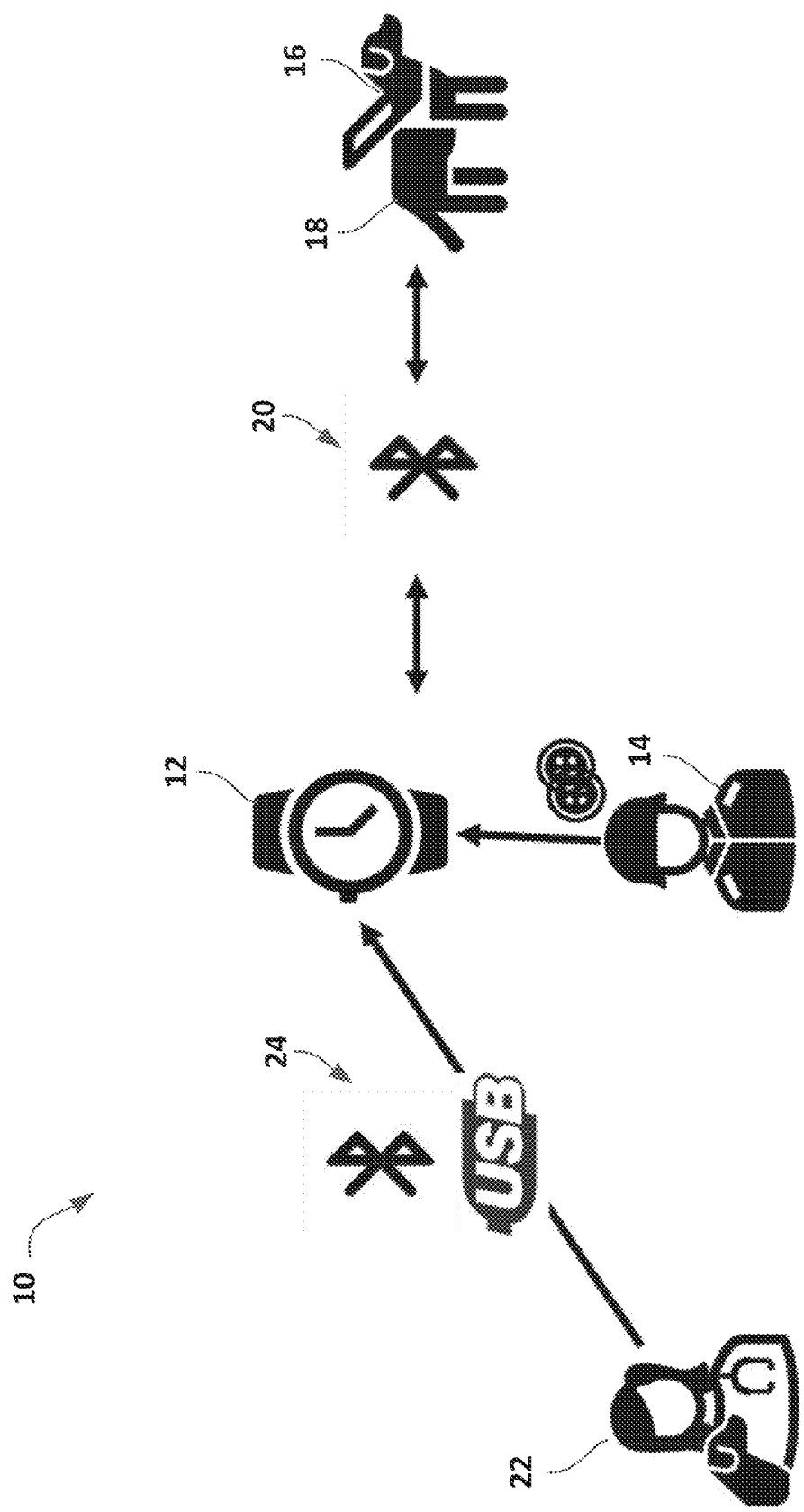
FIG. 1 shows a schematic illustration of one variation of an overview of the system for alerting a service animal of its handler potentially exhibiting PTSD symptoms.

In addressing PTSD-related episodes which may be experienced by a handler 14, a system 10 as shown in the schematic illustration of FIG. 1 may be implemented where the handler 14 may have one or more of physiological parameters monitored by a wearable monitoring device 12. The monitoring device 12 may include any number of devices having a form factor which enables the monitoring device 12 to remain in contact or proximity to the monitoring handler 12 and may include devices such as watches, fitness-tracking devices, bands, necklaces, patches, etc. which incorporate a processor and an optionally integrated user interface which may allow for the handler 14 to access features or functions of the monitoring device 12.

The monitoring device 12 may be configured to noninvasively sense and/or monitor any number of physiological parameters of the handler 14 such as heartrate, blood pressure, respiration rate, etc. and may also incorporate features such as position-tracking using, for instance, accelerometers or location-tracking using, for instance, GPS tracking. In other alternative configurations, the monitoring device 12 may be configured to be worn upon the head, such as a headband, of the handler 14 in which case physiological parameters such as brainwaves of the handler 14 may be detected and monitored. The monitoring device 12 may incorporate a memory component for optionally storing such data (e.g., physiological, position, location, etc.), the handler may not have any outward appearance or characteristics of distress, and may also incorporate a transmitter and/or receiver which enables the transmission or receipt of data or signals through wireless protocols (e.g., Bluetooth®, wireless LAN (IEEE 802.11), ZigBee, Z-Wave, etc.) or any number of wired transmission (e.g., USB, etc.).

The handler 14 may be paired with a service animal 18 which is trained to interrupt PTSD-related episodes in their handler 14 by performing any number of specified tasks. The handler 14 may be the owner of the service animal 18 or may include any individual who is paired with the service animal 18 for which the service animal 18 is specifically trained to perform one or more tasks as described herein. While the service animal 18 is trained to monitor their handler 14 for specific actions or behaviors indicative of a PTSD episode, there are times when the service animal 18 may be distracted by the environment (e.g., loud noises, crowds, etc.) or times when the service animal 18 may be resting or asleep during which times the animal 18 may be unaware of the handler's distress.

Accordingly, an alert device 16 which is specifically wirelessly in communication 20 with the monitoring device 12 worn by the handler 14 may be similarly worn by the service animal 18 such as on a collar, integrated in a vest, patch, or otherwise secured to the body of the service animal 18 or in proximity to the service animal 18. The monitoring device 12 and the alert device 16 may be in wireless communication 20 through any number of wireless protocols as described herein.

In addition to being in wireless communication 20 with the alert device 16, the data stored in the memory of the monitoring device 12 may be available for transmission 24 to one or more third parties 22 such as a physician, counselor, trainer, etc. for receiving the data for monitoring. This data may be transmitted on a regulated schedule or it may be transmitted or obtained by the one or more third parties, for example, on an as-needed basis or a periodic basis such as a weekly or monthly basis. In either case, the data may be used for various purposes such as assessing for the effectiveness of the service animal's training in distracting their handler from an episode or for other reasons such as research purposes.

Figure 2:
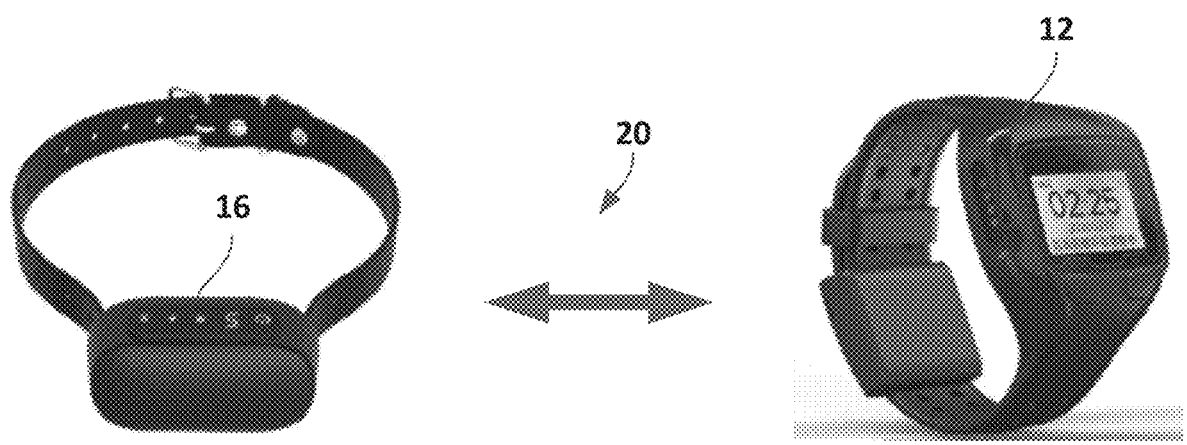
FIG. 2 shows one variation of a wearable monitoring device worn by the handler for wirelessly communicating with an alert device worn by the service animal.

FIG. 2 shows one example of a form factor of the monitoring device 12 shown in the perspective view configured as a watch or fitness-type tracking device which may be worn upon the wrist of the handler 14. One example of the form factor of the alert device 16 is also shown as being mounted upon a collar which may be worn around the neck of the service animal 18. So long as the alert device 16 is noninvasively maintained in relative proximity to the service animal 18, the alert device 16 may be configured into any number of form factors so long as the alert device 16 presents an atraumatic housing which can be comfortably worn by the service animal 18 in a continuous manner except when re-charging. An example of the wireless communication 20 is illustrated by the arrow.

Figure 3:
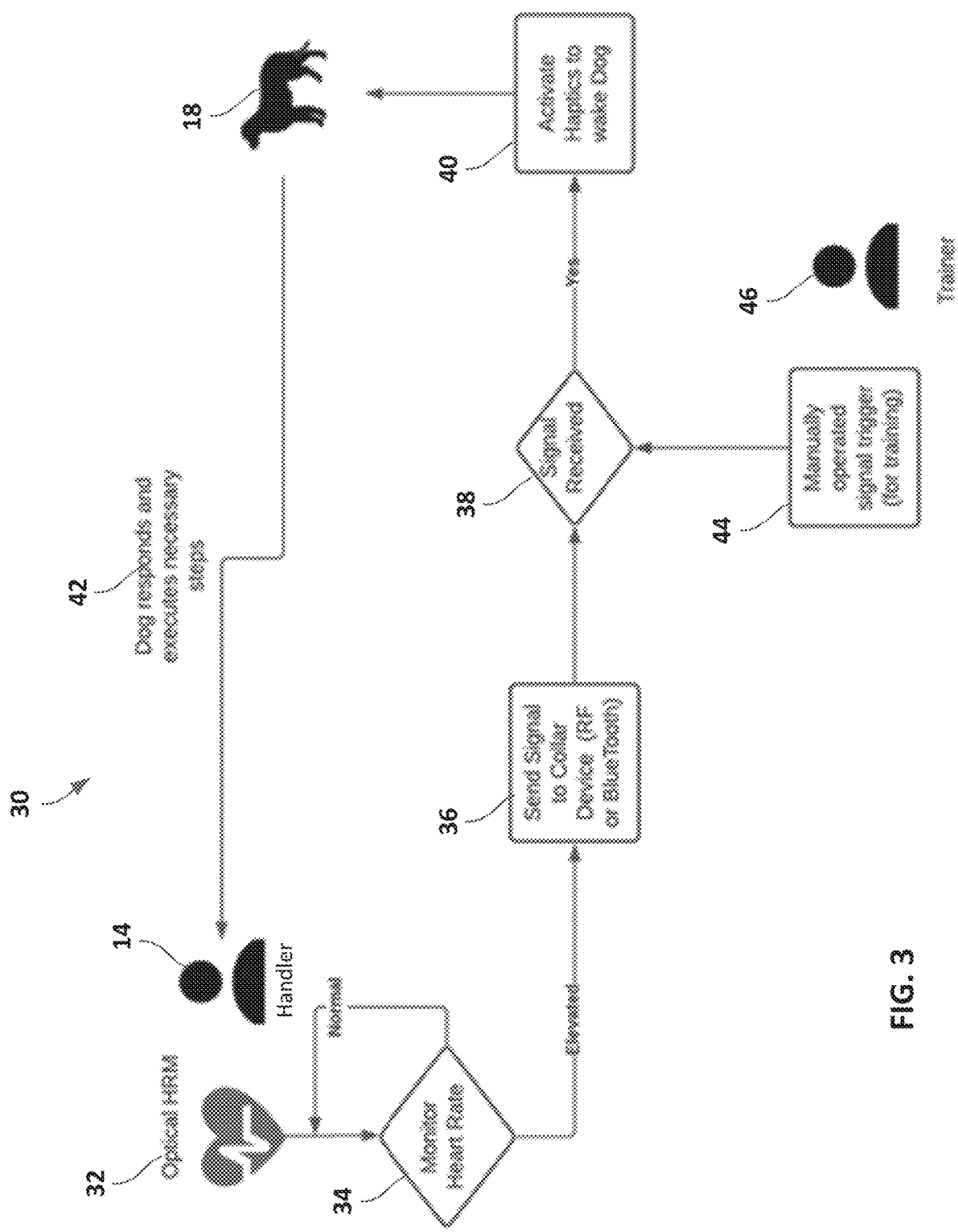
FIG. 3 shows a schematic illustration of one specific embodiment of the alert system.

FIG. 3 shows one variation of how the monitoring device 12 and alert device 16 may be generally utilized in the schematic illustration 30. As described previously, the monitoring device 14 may be worn by the handler 14 while the alert device 16 may be worn by the service animal 18. While any number of physiological parameters of the handler 14 may be monitored, one parameter may include the heartrate 32 of the handler 14 which may be detected and monitored using any number of mechanisms commonly integrated into devices such as optical heartrate monitors 32 worn by users. Such devices typically incorporate light-sensitive photodiodes which are paired with light-emitting devices such as LEDs which transmit light which is reflected or transmitted through the underlying blood vessels of the handler 14 and received by the light-sensitive photodiodes in order to monitor the blood flow of the handler 14.

As the monitoring device 12 monitors the handler's heartrate 34, the monitoring device 12 may remain in a holding status so long as the detected heartrate falls within a normal range. In the event that the heartrate of the handler 14 heartrate becomes elevated for a period of time which falls outside of a predetermined range and their position or location remains static, this may be indicative of the handler 14 experiencing a PTSD-episode. In such a situation, the monitoring device 12 may be triggered to send a signal wirelessly 36 to the alert device 16 worn by the service animal 18. The signal may be received 38 by the alert device 16 which may then activate one of several predetermined alerts 40 (depending upon the mode of the monitoring device 12) as an indicator (e.g., awake or alert) to the service animal 18 to perform one or more tasks or steps 42 which are specifically correlated to the type of alert 40 activated by the alert device 16, as described in further detail herein.

A third-party trainer 46 may initially have access to the monitoring device 12 as well as the alert device 16 for training purposes by which the trainer 46 may manually operate the various predetermined alerts 40 in order to train the service animal 18. In this manner, the trainer 46 may train the service animal 18 to perform a specified task which is correlated to a specified alert received by the service animal 18.

Figure 4:
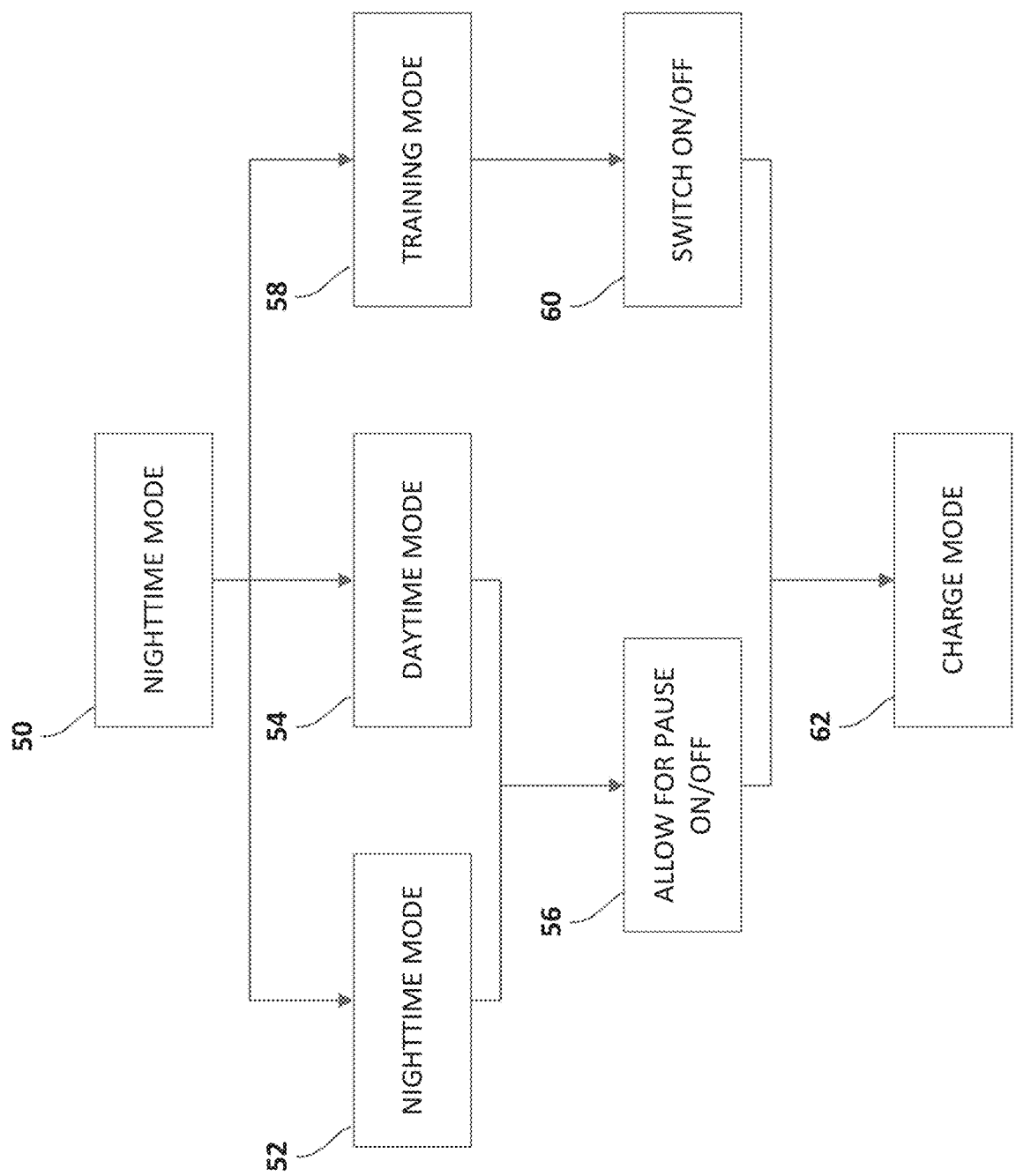
FIG. 4 shows a flow diagram of one variation for placing the system into various modes.

FIG. 4 shows a flow diagram to illustrate how specified tasks to be performed by the service animal 18 may be correlated to specified alerts provided by the alert device 16 to the service animal 18. In one variation, the monitoring device 12 may be configured to reside in one of three different modes: nighttime mode, daytime mode, and training mode. The monitoring device 12 may default to any one of the three modes and in this variation, the device 12 may default in the nighttime mode 50, as shown. In this mode, the processor may be programmed to monitor the heartrate of the handler 14 to track whether the heartrate is within a first monitoring range and over a first specified period of time. The range and period of time may be programmed to reside at default levels or they may be altered so that the levels are typical for the handler 14 when resting or sleeping. For example, the range of the heartrate may be specified to be between 50 to 60 beats per minute when the handler 14 is resting or sleeping. A monitored heartrate that is elevated to be greater than 60 beats per minute for periods of time longer than, for example, five minutes may be an indication that the handler 14 is experiencing a PTSD-episode during rest or sleep (such as a nightmare). In the event that the monitoring device 12 detects the elevated heartrate which continues beyond the specified period of time may trigger the monitoring device 12 to transmit a first nighttime actuation signal to the alert device 16 worn by the service animal 18.

Upon receiving the first nighttime actuation signal, the alert device 16 may be configured to emit a first haptic alert to the service animal 18. An example of a first haptic alert may include a vibration signal that follows a first pattern in a repeating pattern for a specified period of time. Alternatively, rather than a haptic alert, the alert device 16 may be instead configured to emit a first audible alert to the service animal 18. An example of a first audible alert may include an audible signal having a frequency of, e.g., 30-50 kHz, and an amplitude of, e.g., 50 dB, that follows a first pattern, e.g., one second on, one-half second off, in a repeating pattern for a specified period of time. The audible signals described herein may include any range and different types of audible signals which may be audible to both the handler 14 and service animal 18 or those which are audible only to the service animal 18.

The service animal 18 in this situation may be trained to perform a first task which is specifically correlated to this first haptic alert or first audible alert, e.g., tugging a blanket or laying across the handler's body, so as to disrupt the PTSD-episode. If the specified task by the service animal 18 is sufficient to awake the handler 14 or disrupt the episode so that the handler 14 pauses or turns the monitoring device 12 off, the first haptic alert or first audible alert may be stopped.

If the monitored heartrate continues beyond the first specified period or the heartrate itself elevates to a relatively higher specified level, the monitoring device 12 may transmit a second nighttime actuation signal to the alert device 16 such that the alert device 16 then actuates a second haptic alert or second audible alert in which a different haptic or audible alert (e.g., varied in frequency, or amplitude, or pattern, etc. from the first haptic or audible alert) may be emitted by the alert device 16. Upon sensing or hearing the second haptic or audible alert, the service animal 18 may then perform a second task specifically correlated to this second haptic or audible alert, e.g., turning on the lights and licking the handler's face, etc. until the second audible alert is paused or stopped by the handler 14.

Additional haptic or audible alerts may be programmed which vary from one another and may be incorporated depending upon the parameters of the monitored physiologic signals from the handler 14 so long as the service animal 18 is specifically trained in advance by the trainer to perform the specified task correlated to the specified haptic or audible alert. Furthermore, the parameters of the haptic or audible alerts may be varied and the correlated tasks performed by the service animal 18 may also be varied depending upon the training provided to the service animal 18.

The monitoring device 12 may remain in its nighttime mode 52, as shown, or the device 12 may be configured into a daytime mode 54. Whether the nighttime mode 52 or daytime mode 54 is specified, the device 12 may be configured to allow for a pause or on/off of the monitoring or alerts provided.

In the daytime mode 54, the monitoring device 12 may default to a second monitoring range and over a second specified period of time. Like the nighttime mode 52, the daytime mode 54 of device 12 may have a default heartrate range and a default monitoring period both of which may be altered to customize the device 12 for the handler 14. In either case, the heartrate may be specified to be, for example, between 60 to 100 beats per minute when the handler 14 is sitting, walking, or otherwise performing any number of activities when awake. However, a monitored heartrate that is elevated to be greater than, e.g., 100 beats per minute for periods of time longer than, for example, five minutes may be an indication that the handler 14 is experiencing a PTSD-episode such as an anxiety attack when awake. The monitoring device 12 detecting the elevated heartrate which continues beyond the specified period of time may trigger the monitoring device 12 to transmit a first daytime actuation signal to the alert device 16 worn by the service animal 18.

Upon receiving the first daytime actuation signal, the alert device 16 may be configured to emit a second haptic alert to the service animal 18. An example of a second haptic alert may include a vibration signal that follows a second pattern, e.g., one second on, one-half second off, in a repeating pattern for a specified period of time. The service animal 18 in this situation may be trained to perform a second task which is specifically correlated to this second haptic alert, e.g., nudging the handler 14, so as to disrupt the PTSD-episode. If the specified task by the service animal 18 is sufficient to distract the handler 14 or disrupt the episode so that the handler 14 pauses or turns the monitoring device 12 off, the second haptic alert may be stopped. In the event that first and second haptic alerts are used, a singular alert device 16 may be used with the singular actuator as the patterns or other parameters between the first and second haptic alerts are varied to distinguish between the differing modes. In the event that both haptic and audible alerts are used, the alert device 16 may house both the haptic actuator and audible actuator (e.g., speaker).

If the monitored heartrate continues beyond the first specified period or the heartrate itself elevates to a relatively higher specified level, the monitoring device 12 may transmit a second daytime actuation signal to the alert device 16 such that the alert device 16 then actuates a third haptic alert in which a different haptic alert (e.g., varied in frequency, or amplitude, or pattern, etc. from the second haptic alert) may be emitted by the alert device 16. Upon feeling the third haptic alert, the service animal 18 may then perform a second task specifically correlated to this third haptic alert, e.g., licking the hand of the handler 14, etc. until the third haptic alert is paused or stopped by the handler 14.

Additional haptic alerts may be programmed which vary from one another and may be incorporated depending upon the parameters of the monitored physiologic signals from the handler 14 so long as the service animal 18 is specifically trained in advance by the trainer to perform the specified task correlated to the specified haptic alert. Any number of different haptic signals or variations in haptic patterns may be used to alert the service animal 18 to perform any number of daytime-related tasks, as needed.

Because the service animal 18 requires sufficient training to correlate specified tasks to specified audible alerts and/or specified haptic alerts, the monitoring device 12 may also include a training mode 58 which may be selectively switched on/off 60. The training mode 58 may allow for the trainer to selectively actuate a particular mode or specified alerting signal in order to train the service animal 18 to perform correlated specific tasks until the service animal 18 learns each task for each audible and/or haptic alert. The monitoring device 12 may further include a charge mode 62 which may suspend operation of the device 12 during charging of a battery within the device 12.

Figure 5:
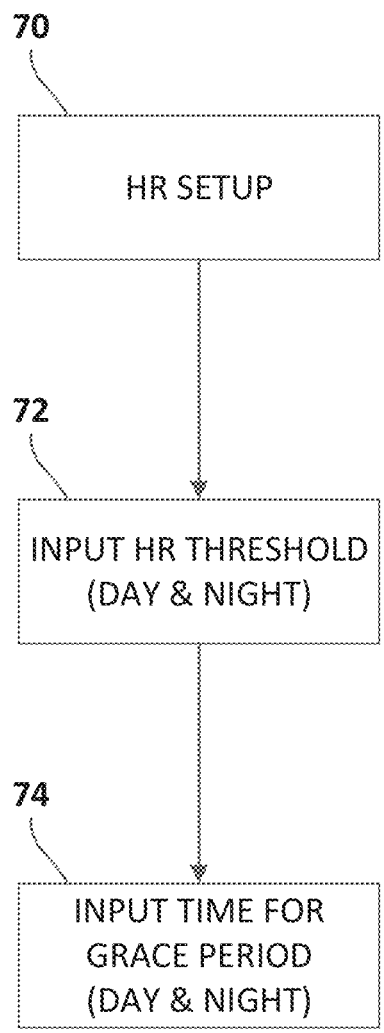
FIG. 5 shows a flow diagram of another variation for entering specified biological parameter thresholds of the handler for monitoring purposes.

As described, while the monitoring device 12 may have default heartrate and monitoring periods for each mode, the monitoring device 12 may also be customized for each handler 14 who may have physiologic parameters which are different from the default settings. For instance, as shown in the flow diagram of FIG. 5, the monitoring device 12 may have a heartrate setup 70 feature which allows for the handler 14 (or other individual) to input 72 different heartrate threshold values for either or both the daytime and nighttime modes. The device 12 may also include a time setup 74 which further allows for the handler 14 to input different grace periods or monitoring time periods for either or both the daytime and nighttime modes.

Figure 6:
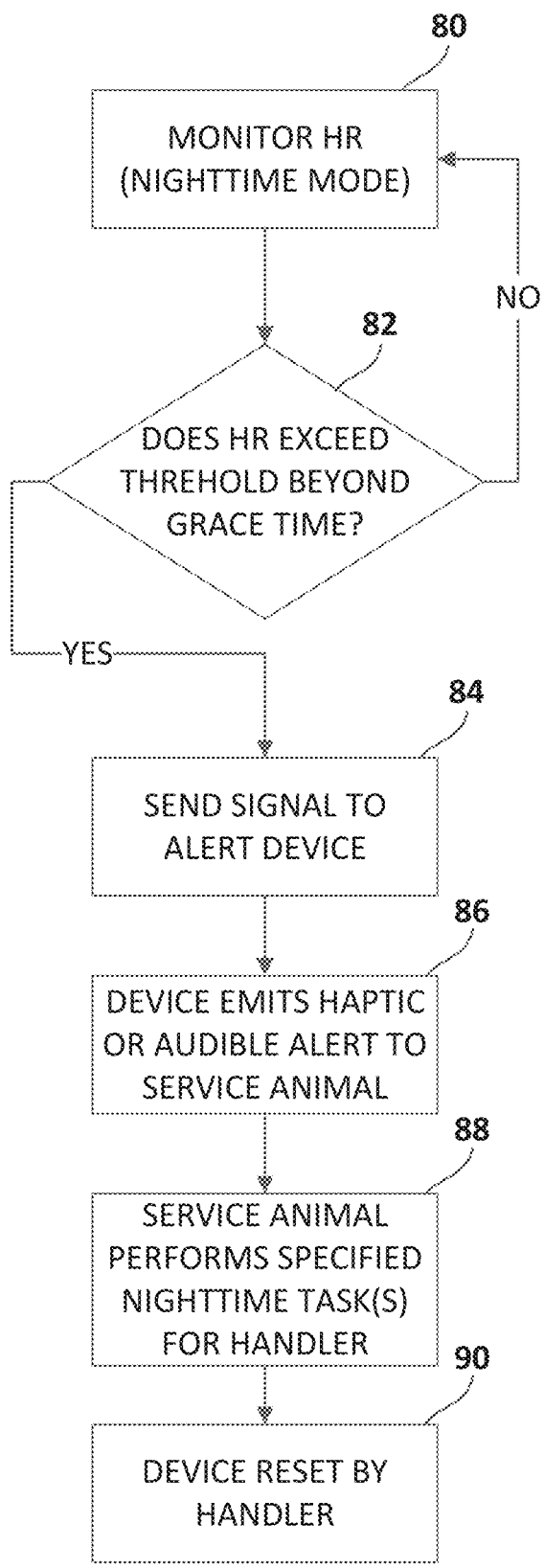
FIG. 6 shows a flow diagram of how the nighttime mode of the system may be configured to monitor and alert the service animal.

As a further illustration of the nighttime mode function of the monitoring device 12, FIG. 6 shows a flow diagram illustrating how the nighttime mode may be implemented. As the handler 14 sleeps, the monitoring device 12 in nighttime mode may monitor the heartrate 80 of the handler 14. If the handler 14 has a heartrate that exceeds the predetermined threshold level for a period of time beyond the preset grace time 82, the monitoring device 12 may be programmed to send an actuation signal to the alert device 84. If the monitored heartrate does not exceed the predetermined threshold level or if an elevated heartrate does not extend beyond the preset grace time, the monitoring device 12 may continue to monitor the handler's heartrate.

However, once the actuation signal has been sent to the alert device 16 worn by the service animal 18, the alert device 16 may emit 86 a haptic alert or an audible alert to the service animal so that the service animal 18 may perform the specified nighttime task or tasks 88 for the handler 14, as described herein. The alert device 16 may continue to provide the haptic or audible alert for a set period of time, e.g., one minute, or until the device 12 is reset 90 by the handler 14. As noted previously, the haptic or audible alerts may be varied and specified tasks to be performed by the service animal 18 may be correlated in a predetermined manner to a particular audible alert.

Figure 7:
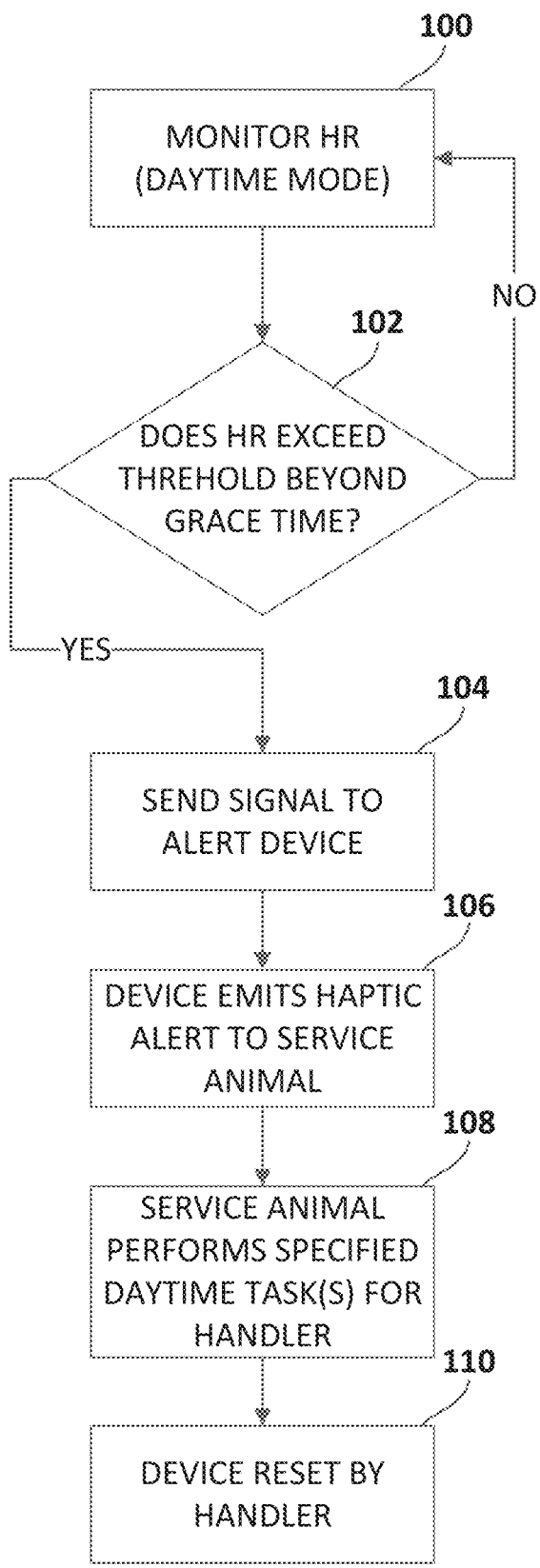
FIG. 7 shows a flow diagram of how the daytime mode of the system may be configured to monitor and alert the service animal.

As a further illustration of the daytime mode function of the monitoring device 12, FIG. 7 similarly shows a flow diagram illustrating how the daytime mode may be implemented. As the handler 14 is awake, the monitoring device 12 in daytime mode may monitor the heartrate 100 of the handler 14. If the handler 14 has a heartrate that exceeds the predetermined threshold level for a period of time beyond the preset grace time 102, the monitoring device 12 may be programmed to send an actuation signal to the alert device 104. If the monitored heartrate does not exceed the predetermined threshold level or if an elevated heartrate does not extend beyond the preset grace time, the monitoring device 12 may continue to monitor the handler's heartrate.

Once the actuation signal has been sent to the alert device 16, the alert device 16 may transmit 106 a haptic alert to the service animal so that the service animal 18 may perform the specified daytime task or tasks 108 for the handler 14, as described herein. The alert device 16 may continue to provide the haptic alert for a set period of time, e.g., one minute, or until the device 12 is reset 110 by the handler 14. As noted previously, the haptic alerts may be varied and specified tasks to be performed by the service animal 18 may be correlated in a predetermined manner to a particular haptic alert.

Figure 8:
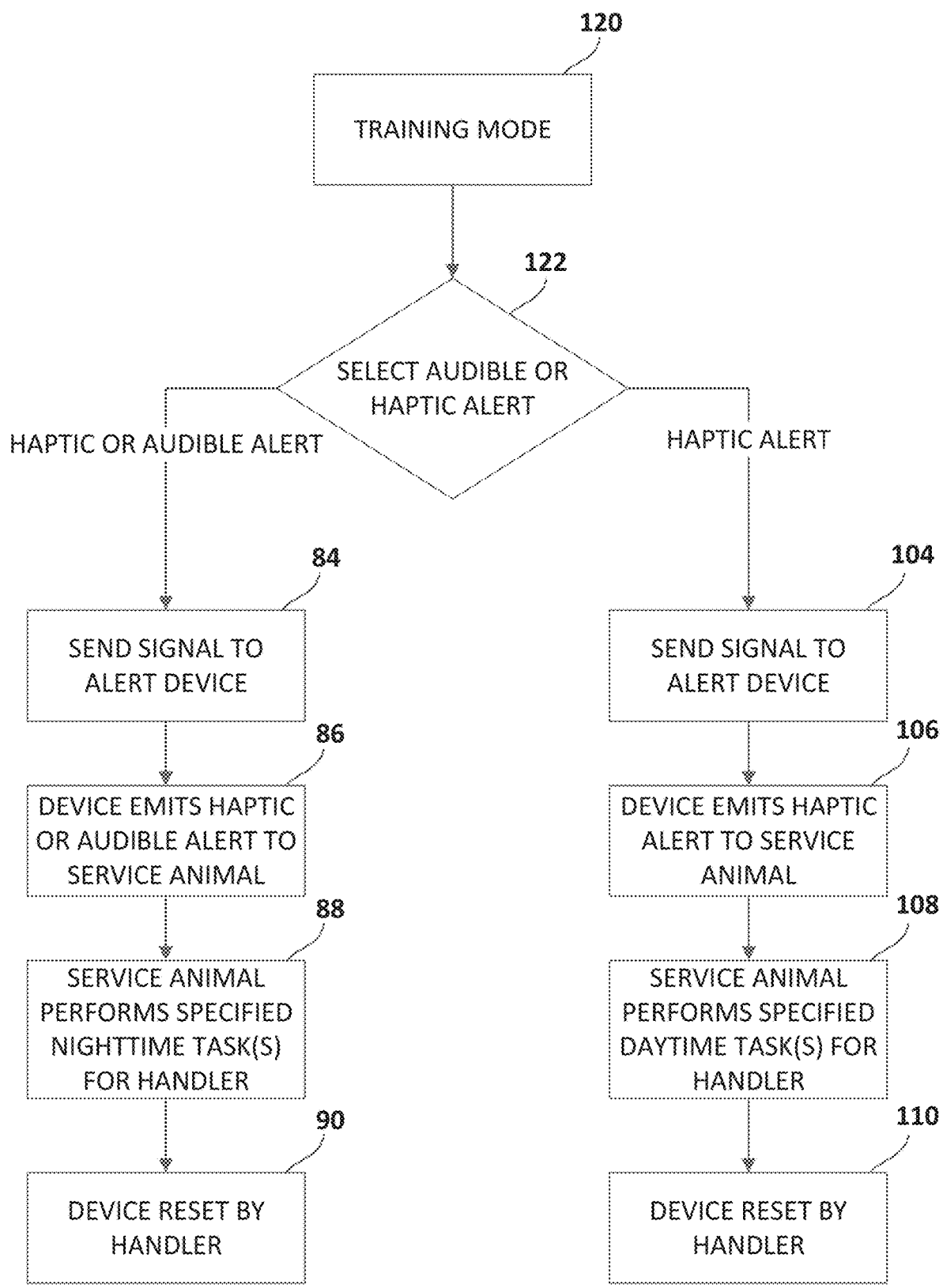
FIG. 8 shows a flow diagram of how the training mode of the system may be configured for training the service animal to respond to specified alerts.

The training mode 120 implementation is further illustrated in the flow diagram of FIG. 8. As described, a particular audible or haptic alert 122 may be preselected via the monitoring device 12 so that the alert device 16 provides the corresponding alert for training purposes. Depending upon whether the audible alert or haptic alert is selected, the signal transmission and corresponding alert may be provided by the alert device 16 so that the service animal 18 may be trained to associate a particular task or tasks to a particular alert or alert type.

The applications of the devices and methods discussed above are not limited to monitoring and disruption of PTSD episodes but may include any number of further treatment applications. Modification of the above-described assemblies and methods for carrying out the invention, combinations between different variations as practicable, and variations of aspects of the invention that are obvious to those of skill in the art are intended to be within the scope of the claims.

What is claimed is:

1. A system for alerting a service animal, comprising:
   an alert device configured to be worn by a service animal and to provide at least a first alert and/or a second alert from the alert device to the service animal;
   a monitoring device configured to be worn by a handler and where the monitoring device is programmed to monitor a physiologic parameter of the handler via at least one sensor, and
   wherein the alert device is actuated when the physiologic parameter is determined to exceed a first predetermined threshold level over a first period of time and/or exceed a second predetermined threshold level over a second period of time such that the alert device provides the first alert or the second alert to the service animal and whereby the first alert is correlated to a first task and the second alert is correlated to a second task in which each of the first task and second task alleviates a mental health condition of the handler to be completed by the service animal.

2. The system of claim 1 wherein the alert device is configured to provide a haptic alert from the alert device in which the haptic alert comprises one or more vibratory patterns correlated to one or more additional tasks to be completed by the service animal.

3. The system of claim 1 wherein the alert device is configured to provide an auditory alert from the alert device.

4. The system of claim 1 wherein the alert device is configured to be secured to a collar worn by the service animal.

5. The system of claim 1 wherein the monitoring device is programmed to monitor a heartrate of the handler.

6. The system of claim 1 wherein the first or second predetermined threshold level comprises a heartrate of the handler when resting or sleeping.

7. The system of claim 6 wherein the first or second predetermined threshold level further comprises a grace period having a predetermined period of time.

8. A method of alleviating a mental health condition in a handler, comprising:
   monitoring a physiologic parameter of the handler over a first period of time and/or over a second period of time via at least one sensor located along a monitoring device worn by the handler;
   determining whether the physiologic parameter exceeds a first predetermined threshold level over the first period of time and/or exceeds a second predetermined threshold level over the second period of time;
   actuating a first alert and/or a second alert via an alert device worn by a service animal alert when the first physiologic parameter exceeds the first predetermined threshold level over the first period of time and/or exceeds the second predetermined threshold level over the second period of time such that the service animal performs a first task which is correlated to the first alert or a second task which is correlated to the second alert in which each of the first task and second task alleviates the mental health condition of the handler.

9. The method of claim 8 wherein monitoring the physiologic parameter comprises monitoring a heartrate of the handler.

10. The method of claim 8 wherein the predetermined threshold further comprises a grace period having a predetermined period of time.

11. The method of claim 8 wherein the first or second predetermined threshold level comprises a heartrate of the handler when resting or sleeping.

12. The method of claim 8 wherein the first or second predetermined threshold level comprises a heartrate of the handler when awake.

13. The method of claim 8 wherein the alert comprises a haptic alert in which the haptic alert comprises one or more vibratory patterns correlated to one or more additional tasks to be completed by the service animal.

14. The method of claim 8 wherein the method comprises alleviating a PTSD-episode experienced by the handler.

15. The method of claim 8 wherein the method comprises alleviating anxiety experienced by the handler.

* * * * *